United States Patent [19]

Matsui et al.

[11] Patent Number: 4,820,264
[45] Date of Patent: Apr. 11, 1989

[54] INFUSION INSTRUMENT

[75] Inventors: Mizuo Matsui, Urawa; Fumio Ohtomo, Tokyo; Koji Sato, Tokyo; Yoshihiro Takahashi, Tokyo, all of Japan

[73] Assignee: Tokyo Kogaku Kikai Kabushiki Kaisha, Tokyo, Japan

[21] Appl. No.: 857,171

[22] Filed: Apr. 29, 1986

[30] Foreign Application Priority Data

May 1, 1985 [JP] Japan .................. 60-92343
May 1, 1985 [JP] Japan .................. 60-92344
Jun. 20, 1985 [JP] Japan .................. 60-132958

[51] Int. Cl.$^4$ .............................................. A61N 1/30
[52] U.S. Cl. .................................. 604/21; 604/117; 604/174; 604/272; 604/294; 128/303.1
[58] Field of Search .............. 128/305, 303.1; 604/21, 604/93, 257, 290, 294, 272, 117, 174, 175, 264, 35, 27, 44

[56] References Cited

U.S. PATENT DOCUMENTS

| | | | |
|---|---|---|---|
| 3,659,607 | 5/1972 | Banko | 128/305 |
| 3,821,510 | 6/1974 | Muncheryan | 604/21 |
| 4,222,375 | 9/1980 | Martinez | 604/20 |
| 4,269,192 | 5/1981 | Matsuo | 604/21 |
| 4,311,138 | 1/1982 | Sugarman | 604/21 |
| 4,331,130 | 5/1982 | Lewicky | 128/305 |
| 4,551,129 | 11/1985 | Coleman et al. | 604/21 |
| 4,567,882 | 2/1986 | Heller | 604/21 |
| 4,596,552 | 6/1986 | De Vries | 604/35 |

Primary Examiner—C. Fred Rosenbaum
Assistant Examiner—Mario Costantino
Attorney, Agent, or Firm—Foley & Lardner, Schwartz, Jeffery, Schwaab, Mack, Blumenthal & Evans

[57] ABSTRACT

An infusion instrument comprises an infusion device for supplying intracular irrigating through an input end thereof, an infusion passage thereof and an insertion end thereof into an eyeball, an illumination unit including a light source for illuminating an inside portion of the eyeball, and a light transmitting element having a first end connected to the light source and a second end for transmitting a light from the light source to the eyeball. At least the second end of the light transmitting element is arranged in the infusion passage.

20 Claims, 11 Drawing Sheets

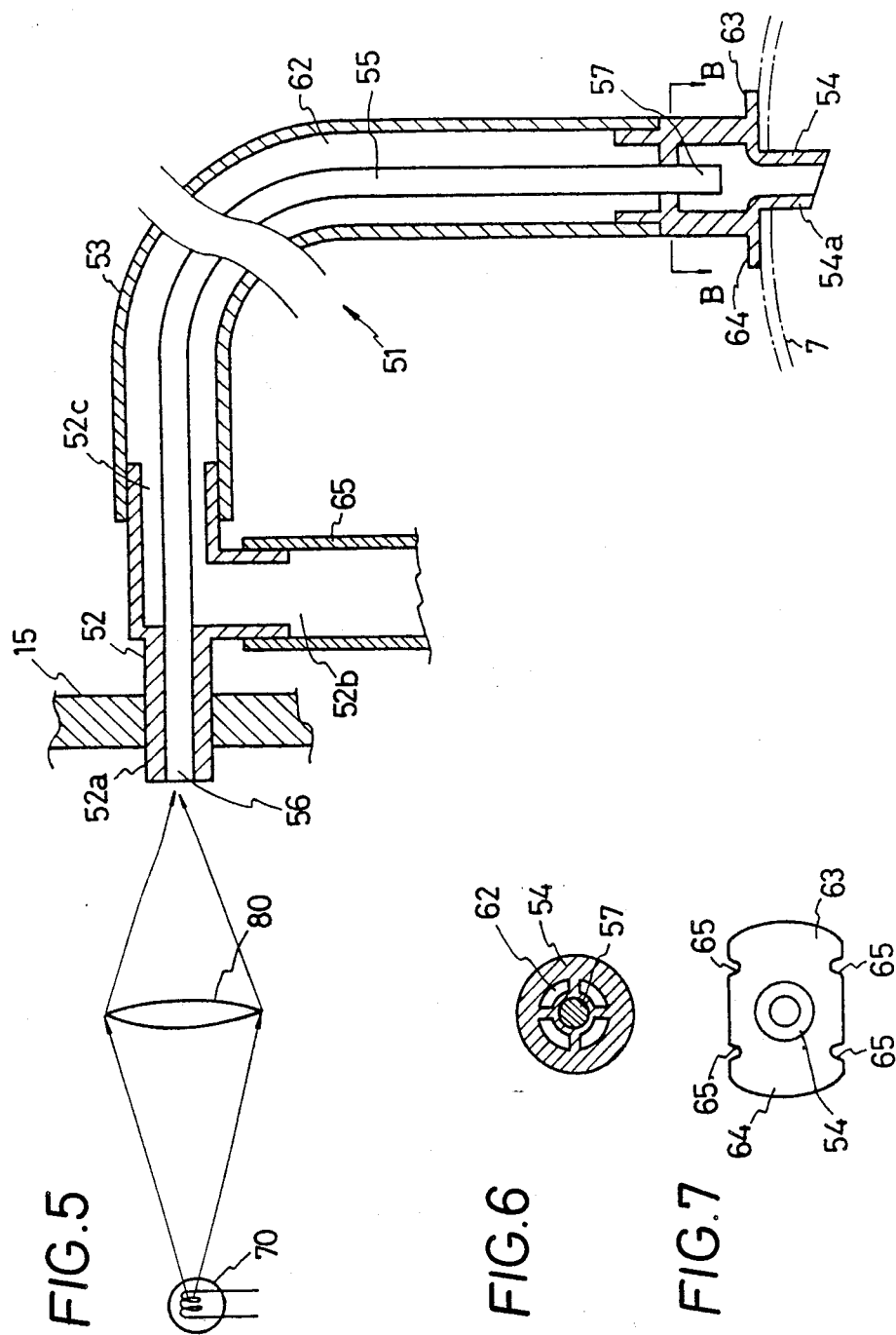

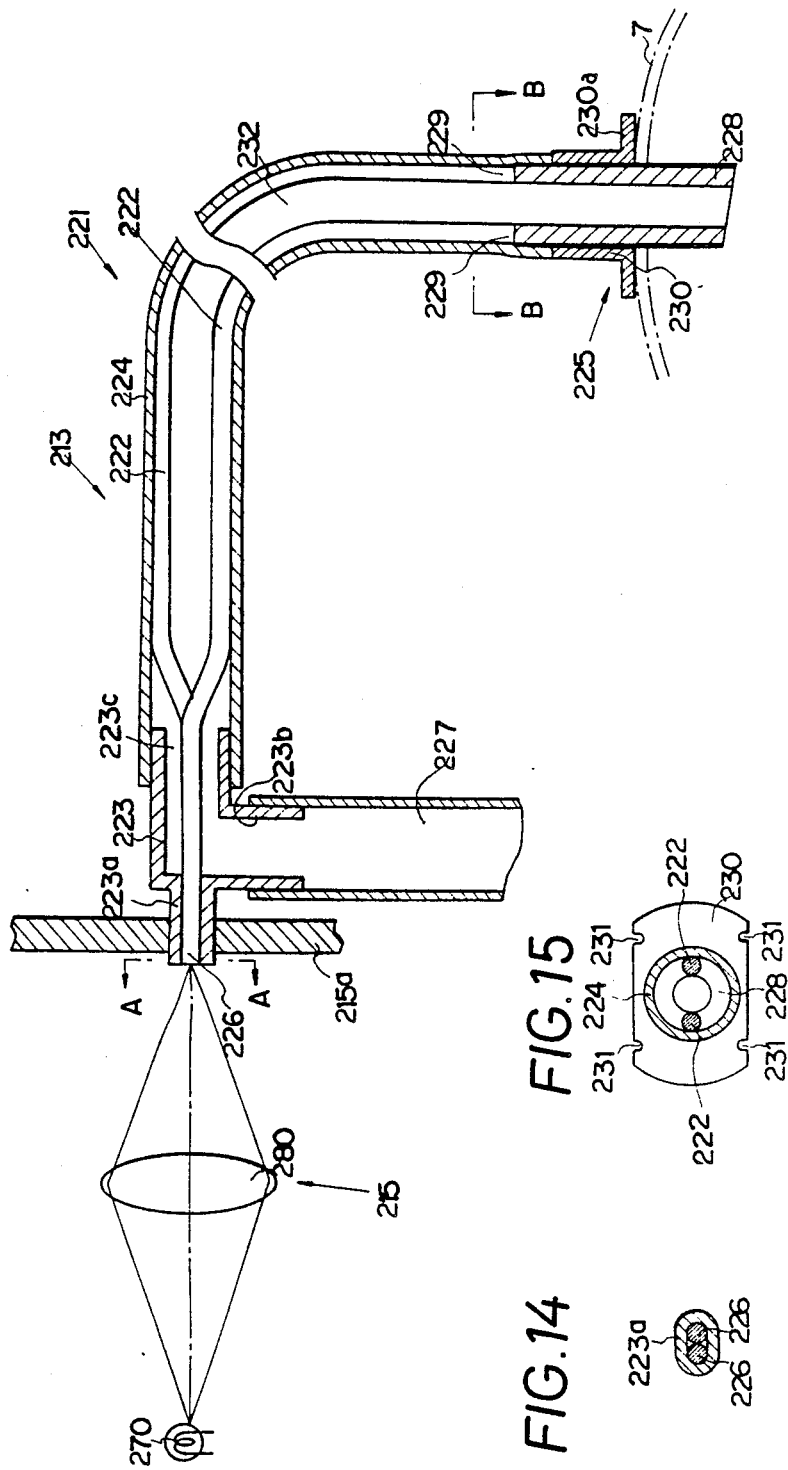

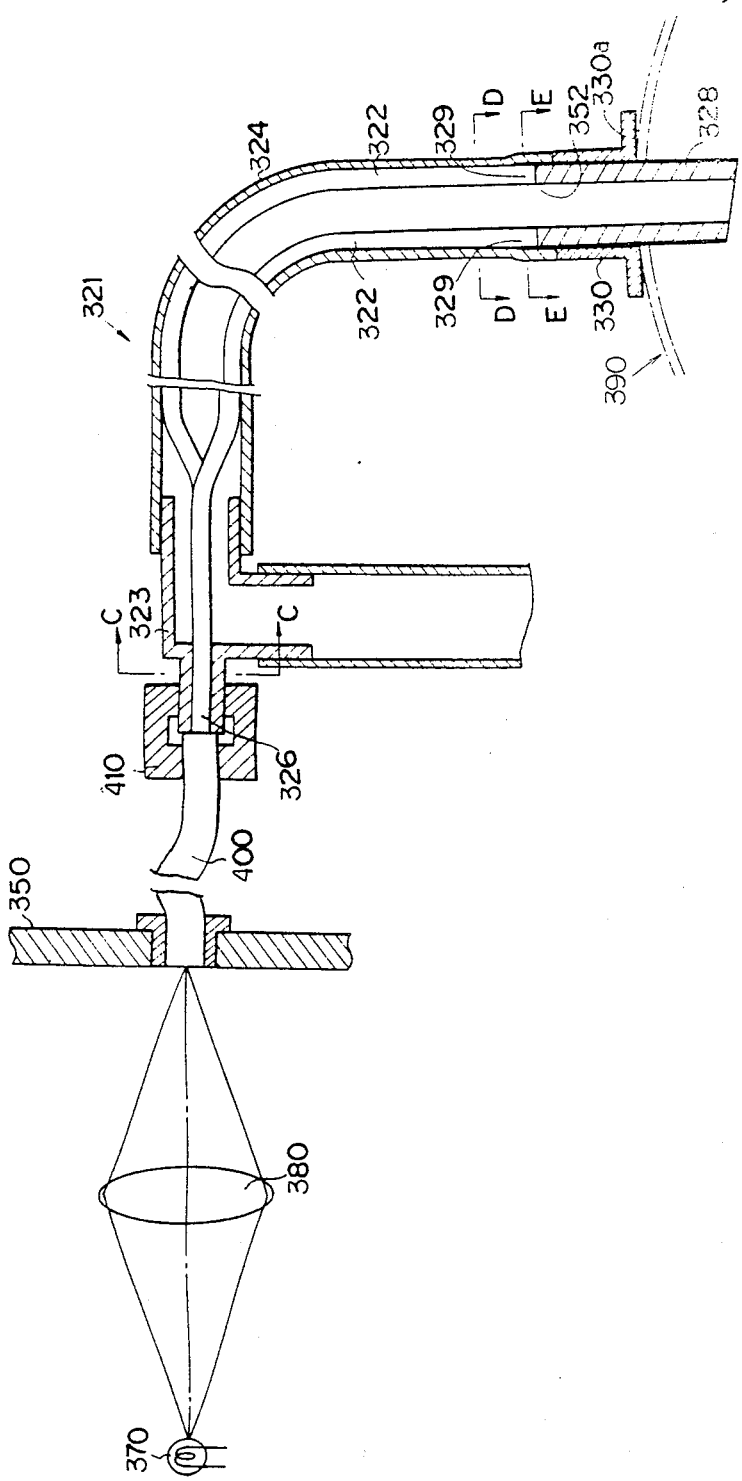

INFUSION INSTRUMENT

BACKGROUND OF THE INVENTION

This invention relates to an infusion instrument for use in vitrectomy and in particular relates to an infusion instrument having an illumination unit for illuminating the inside of an eyeball.

FIGS. 21 and 22 show a conventional operation condition in which a prior art infusion instrument is used in vitrectomy, for instance, in order to cut an opaque portion of the vitreous between a lens 1p and a retina 2p so as to be replaced with a transparent liquid such as intraocular irrigating solutions whereby light can properly reach the retina 2p through the lens 1p or in order to cut a tissue proliferation formed in front of the retina 2p so that light can properly reach the retina 2p.

It is well-known that infusion, cutting, suction and illumination are indispensable to vitrectomy. In a conventional operation, a cutter 4p and a tool 5p are inserted into the scleral 7p of the eyeball 3p at a distance of about 4 mm from the limbus cornea 6p. The cutter 4p has a passage for the suction purpose therein. The tool 5p has an infusion tube 8p and a plurality of optical fibers 9p for the illumination purpose as shown in FIG. 22.

In operation, the cutter 4p and the tool 5p are held by hands, respectively. While the light from the optical fibers 9p illuminates the inside of the eyeball 3p, an opaque portion of the vitreous body 10p is cut by the cutter 4p. At the same time, the intraocular irrigating solution is infused into the eyeball while the cut portion is sucked through the passage of the cutter 4p to the outside of the eyeball 3p. A predetermined intraocular pressure in the eyeball 3p can be maintained by the intraocular irrigating solution.

In the conventional infusion instrument, however, the sectional area of the tool 5p must be large because the plural optical fibers 9p are arranged around the infusion tube 8p. Thus, collapse of the eye is apt to take place when the tool 5p is drawn out from the eyeball 3p.

If the tool 5p is set small in section, then the inside of the eyeball is not illuminated to a desired degree, and a sufficient volume of intraocular irrigating solution does not flow through the infusion tube 8p.

SUMMARY OF THE INVENTION

The object of this invention is to provide an infusion instrument for use in vitrectomy in which the inside of an eyeball can be sufficiently illuminated and collapse of the eye can be avoided.

According to this invention, an infusion instrument comprises an infusion means for supplying intraocular irrigating solution through an input end thereof, an infusion passage thereof and an insertion end thereof into an eyeball, an illumination unit including a light source for illuminating an inside portion of the eyeball, and a light transmitting means having a first end connected to the light source and a second end for transmitting light from the light source to the eyeball. At least the second end of the light transmitting means is arranged in the infusion passage so as to illuminate the inside portion of the eyeball. For example, a majority of the light transmitting means is placed within the infusion passage of the infusion means. Only an end of the light transmitting means may be placed near or at a place where the light from the light source reaches the inside of the eyeball through the insertion end within the infusion means.

Preferably, the light transmitting means is a plastic optical fiber.

BRIEF DESCRIPTION OF THE DRAWINGS

FIG. 5 is a sectional view showing a portion of an infusion means and an illumination unit used in the infusion instrument shown in FIG. 4;

FIG. 6 is a sectional view taken along the line B—B of FIG. 5;

FIG. 7 is a bottom view showing an insertion member in the infusion instrument shown in FIG. 4;

FIG. 13 is a sectional view showing an infusion means and its related members used in the infusion instrument shown in FIG. 12;

FIG. 14 is a sectional view taken along the line A—A of FIG. 13;

FIG. 15 is a sectional view taken along the line B—B of FIG. 13;

FIG. 16 is a sectional view showing an infusion means and its related members according to a sixth embodiment of this invention;

EMBODIMENT 1

Figure 1:
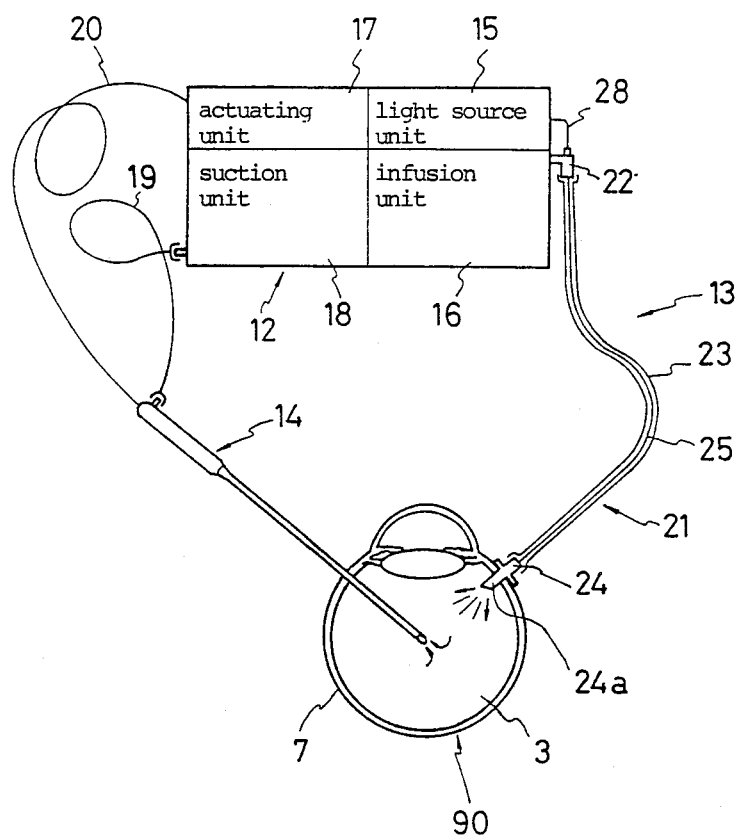
FIG. 1 is an explanatory view showing an operation condition in which a pipe-like infusion instrument and its related parts according to a first embodiment of this invention are used in vitrectomy.
Figure 2:
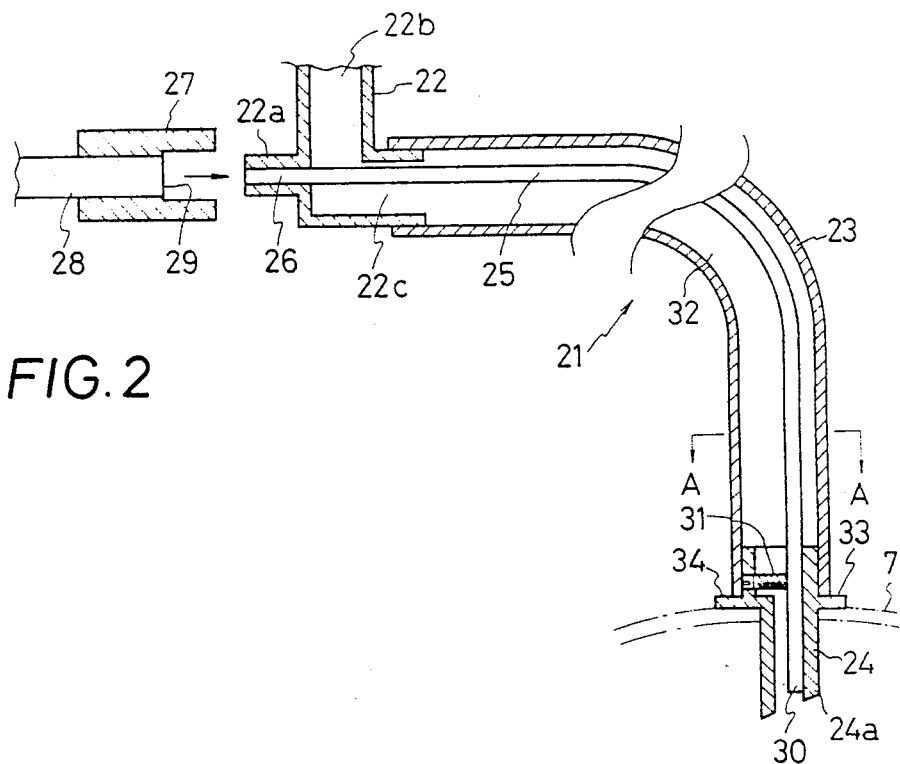
FIG. 2 is an enlarged sectional view showing an infusion means in the infusion instrument shown in FIG. 1.
Figure 3:
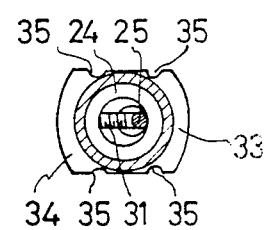
FIG. 3 is a sectional view taken along the line A—A of FIG. 2.
Figure 4:
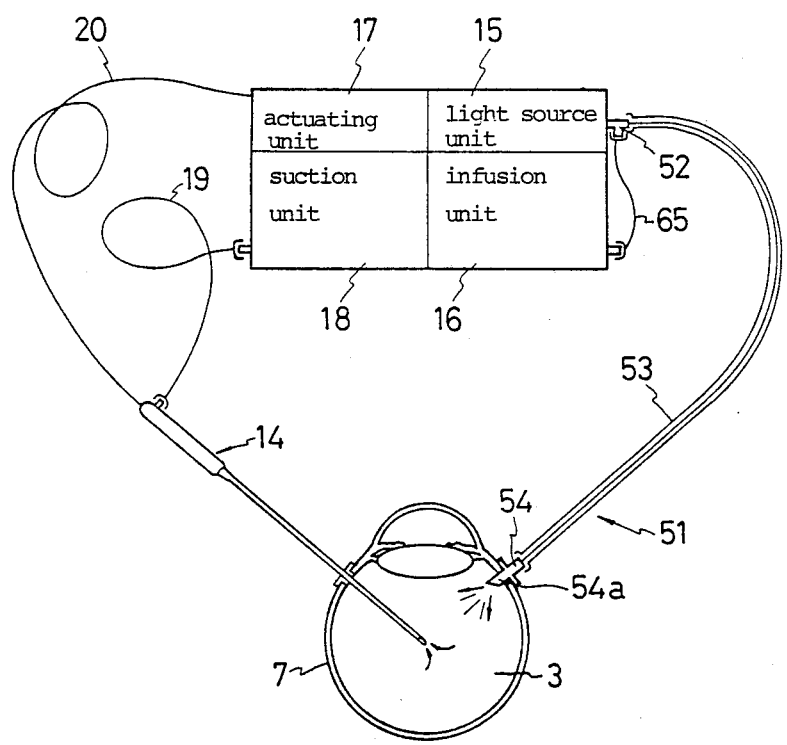
FIG. 4 is an explanatory view showing an operation condition in which an infusion instrument according to a second embodiment of this invention is used in vitrectomy.

FIGS. 1 to 3 show a first embodiment of this invention.

A vitrectomy apparatus includes an external means 12, an infusion instrument 13 according to this invention and a cutter 14. The external means 12 is composed of an actuating unit 17 and a suction unit 18. The cutter 14 is equipped with a motor (not shown) for cutting the vitreous body 3 by its inner blade means (not shown). A suction passage is placed in the cutter 14 and connected by way of a suction pipe 19 to the suction unit 18. The motor is connected through an electric cable 20 to the actuating unit 17.

The infusion instrument 13 includes a light source unit 15 equipped with a light source therein, an infusion means 21, a first light transmitting means 25 and a second light transmitting means 28 as shown in FIGS. 1 and 2.

The infusion means 21 has a first member 22, a pipe-like second member 23, a pipe-like insertion member 24 and an infusion unit 16.

The first light transmitting means 25 is placed within the second member 23 of the infusion means 21 between the first member 22 and the insertion member 24. Preferably, the first light transmitting means 25 is an optical fiber made of a glass or plastics having a good flexibility or resiliency. The pipe-like second member 23 is also made of a flexible or resilient material. If the second member 23 and the first light transmitting means 25 are flexible or resilient, an eyeball 90 does not receive an overpressure due to their spring force when the infusion means 21 is sutured to the eyeball 90 in operation.

The first member 22 has three parts: a small-diameter joint portion 22a, a relatively large-diameter connecting portion 22b connected to the infusion unit 16 and a further relatively large-diameter joint portion 22c inserted into one end of the second member 23. An input end 26 of the first light transmitting means 25 is inserted into the joint portion 22a.

The joint portion 22a is to be joined to a connector 27 into which an output end 29 of the second light transmitting means 28 is inserted. The second light transmitting means 28 is preferably an optical fiber made of a glass or plastics and has a larger diameter than that of the first light transmitting means 25. Thus, even if the first and second light transmitting means 25, 28 are misaligned to some minor degree, light can be properly transmitted therebetween. An input end of the second light transmitting means 28 is connected to the light source unit 15.

An insertion member 24 such as an infusion cannula is inserted into the other end of the second member 23. An insertion end 24a of the insertion member 24 has an inclined end surface so that it can be easily inserted into the eyeball 90. The inner diameter of the insertion end 24a is smaller than that of the second member 23 and larger than the outer diameter of the first light transmitting means 25.

The first light transmitting means 25 extends from the first member 22 through the second member 23 to the insertion member 24. The first light transmitting means 25 is fixed at its output end 30 to the insertion member 24. That is, the first light transmitting means 25 is fixed to an inner wall of the insertion member 24 by means of a bolt 31 fixed to the insertion member 24 as best shown in FIG. 3.

An infusion passage 32 for the intraocular irrigating solution which is a transparent liquid extends from the interior of the first member 22 through the interior of the second member 23 to the interior of the insertion member 24. Although at least the output end 30 of the first light transmitting means 25 should be placed within the infusion passage 32, a majority of the first light transmitting means 25 is preferably positioned within the infusion passage 32.

The insertion member 24 has two flange portions 33, 34 projecting from its periphery. Four recesses 35 are formed in the flange portions 33, 34 for hooking strands or threads when the infusion means 21 is sutured to the scleral 7 of the eyeball 90.

In operation, the scleral 7 is incised at two portions thereof in such a manner that the cutter 14 and the insertion member 24 can be inserted into the eyeball therethrough. If desired, a further portion of the scleral 7 is incised for forceps and so on. The flange portions 33, 34 are fixed to the scleral 7 by the threads or strands sutured thereto.

The light source in the light source unit 15 is switched on to illuminate the inside of the eyeball 90 by way of the first and second light transmitting means 25, 28. An opaque portion of the vitreous body is cut by the cutter 14. The infusion unit 16 is actuated so as to infuse the intraocular irrigating solution through the infusion passage 32 and the insertion member 24 into the eyeball 90. Also, the suction unit 18 is actuated so as to suck both the cut portion and the intraocular irrigating solution.

After the cutting and suction, the vitreous cavity is filled with the intraocular irrigating solution thereby to obtain a predetermined intraocular pressure therein.

At the end of the operation, the insertion member 24 and the cutter 14 are drawn out and then the incised portions are sutured.

No cover for the first light transmitting means 25 is additionally required because the first light transmitting means 25 is placed within the infusion passage 32 and both the second member 23 and the insertion member 24 forming an extending portion of the infusion passage 32 function as a cover for the first light transmitting means 25. Thus, the sectional area of the insertion end 24a can be set relatively small. As a result, collapse of the eye can be avoided after the insertion end 24a is drawn out from the eyeball 90. In addition, the insertion member 24 can be light in weight and small in size so that it can be sutured directly onto the eyeball 90. Also, it is not necessary to support the infusion means 21.

While the intraocular irrigating solutions flow through the infusion passage 32, even if a strong light from the light source reaches the first light transmitting means 25, the intraocular irrigating solutions function as a coolant whereby deformation of the first light transmitting means 25 can be avoided.

EMBODIMENT 2

FIGS. 4 to 7 show a second embodiment of this invention which is substantially the same as the first embodiment of FIGS. 1 to 3 except for the construction of infusion means 51. The same references designate the same or corresponding members or parts.

In the second embodiment of FIGS. 4 to 7, light is transmitted through a single light transmitting means 55 having no joint portion. The light transmitting means 55 is preferably an optical fiber made of a glass or plastics.

The infusion means 51 has a T-shape along the cross section of first member 52, a tube-like second member 53, and an insertion member 54 such as an infusion cannula. A connecting portion 52a of the first member 52 is inserted into a side wall of the light source unit 15. An input end 56 of the light transmitting means 55 is inserted into the connecting portion 52a and faces toward the light source 70 within the light source unit 15. A relay lens 80 is disposed between the light source 70 and the input end 56 of the light transmitting means 55. An image from the light source 70 is projected at the input end 56 thereof.

A connecting portion 52b of the first member 52 is connected by way of a connecting tube 65 to the infusion unit 16. A joint portion 52c of the first member 52 is inserted into one end of the second member 53.

The insertion member 54 is inserted into the other end of the second member 53. An insertion end 54a of the insertion member 54 has an inclined end surface so as to be easily inserted into the scleral 7. The inner surface of the insertion member 54 has a specular reflection of an excellent light reflection rate. The output end 57 of the light transmitting means 55 is positioned within the insertion member 54 and is fixed thereto as shown in FIG. 6. The outer diameter of the insertion end 54a is smaller than that of the second member 53 as shown in FIG. 5. The insertion member 54 has two extending portions 63, 64 like a flange formed with recesses 65 for hooking strands or threads as shown in FIG. 7.

The first member 52, the second member 53 and the insertion member 54 are made of a synthetic resin or the like. The second member 53 is preferably transparent and resilient.

An infusion passage 62 has such a length that it can be arranged from the first member 52 through the second member 53 to the insertion member 54. A majority of the light transmitting means 55 is positioned within the infusion passage 62.

The operation of the second embodiment will not be described because it is substantially the same as that of the first embodiment.

EMBODIMENT 3

Figure 8:
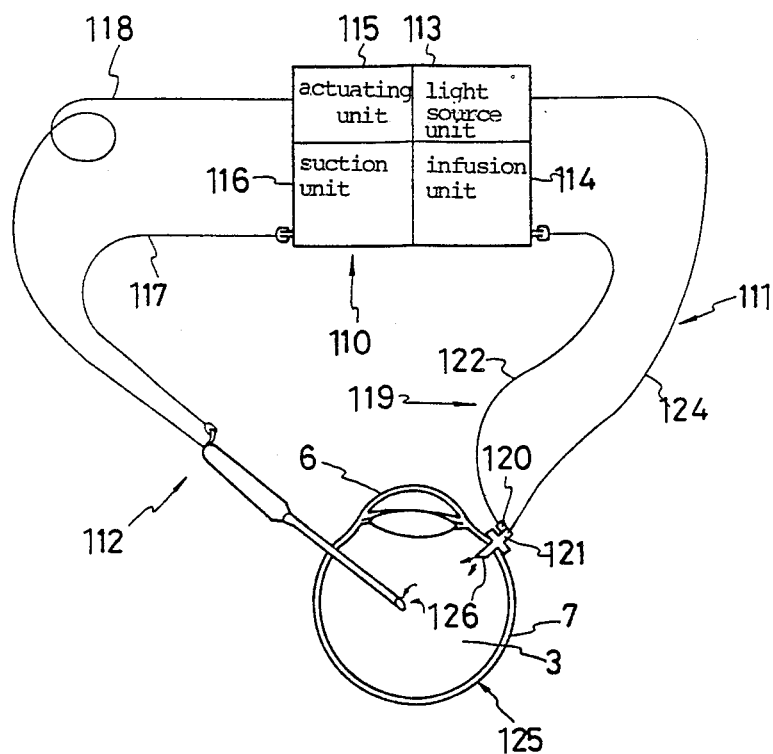
FIG. 8 is an explanatory view showing an operation condition in which an infusion instrument according to a third embodiment of this invention is used in vitrectomy.
Figure 9:
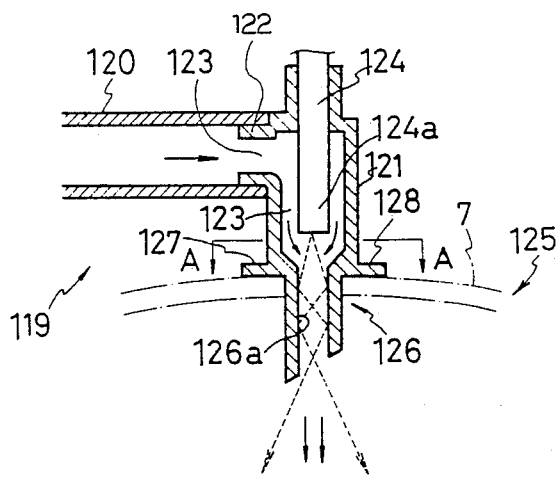
FIG. 9 is a sectional view showing a portion of an infusion means in the infusion instrument shown in FIG. 8 which is sutured to an eyeball.
Figure 10:
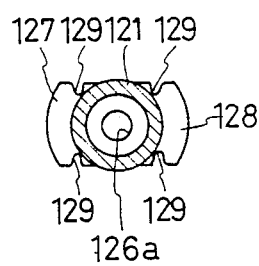
FIG. 10 is a sectional view taken along the line A—A of FIG. 9.

FIGS. 8 to 10 show a third embodiment of this invention.

A vitrectomy apparatus includes an external means 110, an infusion instrument 111 according to this invention and a cutter 112. The external means 110 is composed of an actuating unit 115 and a suction unit 116. The cutter 112 is equipped with a motor (not shown) so as to cut the vitreous body 3 by its inner blade means (not shown). A suction passage is placed in the cutter 112 and connected by way of a suction pipe 117 to the suction unit 116. The motor is connected through an electric cable 118 to the actuating unit 115.

The infusion instrument 111 includes a light source unit 113 equipped with a light source therein, an infusion means 119 and a light transmitting means 124 as shown in FIGS. 8 to 10.

The infusion means 119 has a tube-like first member 120, a pipe-like second member 121, an infusion pipe 122 and an infusion unit 114.

The resilient or flexible infusion pipe 122 connects one end of the first member 120 to the infusion unit 114 and is preferably made of a transparent synthetic resin. An L-shape section of infusion passage 123 is formed in the first member 120 and the second member 121. The output end 124a of the light transmitting means 124 is inserted into one end of the second member 121 and positioned within the infusion passage 123 near an inner wall 126a of an insertion end 126 thereof. The light transmitting means 124 is preferably an optical fiber made of a glass or plastics having a good resiliency. The input end of the light transmitting means 124 is connected to the light source unit 113.

The insertion end 126 of the second member 121 has an inclined end surface so as to be easily inserted into the eyeball 125. The inner diameter of the insertion end 126 is smaller than that of the infusion passage 123 of the second member 121 and substantially corresponds to the outer diameter of the light transmitting means 124.

The inner surface 126a of the insertion end 126 of the second member 121 has a specular reflection so that the light from the output end 124a of the light transmitting means 124 can be reflected at a high rate. For example, an aluminum-deposited layer may be formed thereon. The second member 121 functions as both an infusion passage and a light guide passage.

The second member 121 has two extending portions 127, 128 such as an infusion cannula projecting from its periphery which are formed with four recesses 129 for hooking strands or threads when the second member 121 is sutured onto the scleral 7 of the eyeball 125.

In operation, the scleral 7 is incised at a distance of about 4 mm from a limbus cornea in such a manner that the cutter 112 and the infusion means 119 can be separately inserted into the eyeball 125 therethrough. If desired, the scleral 7 is further incised for forceps and so on. The extending portions 127, 128 are fixed to the scleral 7 by the threads or strands sutured thereto.

The light source in the light source unit 113 is switched on to transmit a light by way of the light transmitting means 124 to the second member 121. The light from the output end 124a of the light transmitting means 124 is reflected by the inner wall 126a of the insertion end 126 so as to illuminate the vitreous body 3 as shown by dotted lines in FIG. 9. An opaque area of the vitreous body 3 is cut by the cutter 112 under illumination from the light transmitting means 124. At the same time, the cut portion is sucked through the cutter 112 and the pipe 117 into the suction unit 116. Also, the intraocular irrigating solution from the infusion unit 114 is infused through the infusion pipe 122 and the infusion passage 123 into the eyeball 125.

After the cutting and suction, the vitreous cavity is filled with the intraocular irrigating solution thereby to obtain a predetermined intraocular pressure therein.

At the end of the operation, the insertion end 126 and the cutter 112 are drawn out and then the incised portions are sutured.

During the operation, the inside of the eyeball 125 is illuminated enough to obtain a visual field therein for operation. The diameter of the light transmitting means 124 can be large to such a degree that the intraocular irrigating solution can smoothly flow through the infusion passage 123. Also, as the inner wall 126a of the insertion end 126 has a good reflection, the light from the output end 124a can be effectively transmitted to the inside of the eyeball 125 without loss.

The light transmitting means 124 itself is not inserted into the eyeball 125. The output end 124a of the light transmitting means 124 is positioned within the second member 121 at or near a place where the light from the light source reaches the inside of the eyeball 125 through the insertion end 126 within the infusion passage 119. The outer diameter of the insertion end 126 can be set relatively large without regard to a size of the light transmitting means 124. The inner diameter of the insertion end 126 can be set large to such a degree that a predetermined volume of intraocular irrigating solution can be infused into the eyeball 125.

When the insertion end 126 is drawn out, collapse of the eye can be avoided because the outer diameter of the insertion end 126 is small.

EMBODIMENT 4

Figure 11:
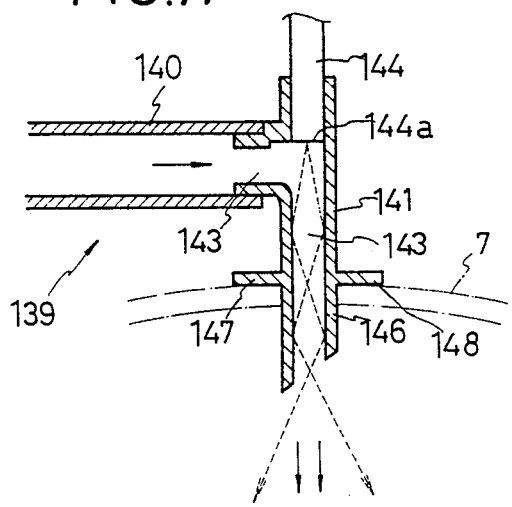
FIG. 11 is a sectional view showing an essential portion of an infusion means according to a fourth embodiment of this invention, corresponding to FIG. 9.

FIG. 11 shows a fourth embodiment of this invention which is substantially the same as the third embodiment of FIGS. 8 to 10 except the construction of the infusion means. The same references designate the same or corresponding members or parts.

In the fourth embodiment of FIG. 11, an infusion means 139 has a pipe-like first member 140 and a second member 141 connected thereto. The first member 140 is similar in shape to the first member 120 of FIG. 9. The second member 141 differs in form from the second member 121 of FIG. 9. An L-shape section of infusion passage 143 is formed in the first and second members 140, 141.

The inner diameter of the infusion passage 143 of the second member 141 is the same as that of the insertion end 146. An output end 144a of the light transmitting means 144 is inserted into one end of the second member 141. The light transmitting means 144 is preferably an optical fiber made of a glass or plastics. The output end 144a thereof constitutes an extending portion of the infusion passage 143 and does not project into the infusion passage 143.

The second member 141 and the insertion end 146 have a continuous inner wall of a good reflection as in the third embodiment of FIG. 9.

Two extending portions 147, 148 such as an infusion cannula are formed at a periphery of the second member 141.

The infusion means 139 of FIG. 11 is used like in the infusion means 119 of FIGS. 8 to 10.

EMBODIMENT 5

FIGS. 12 to 15 show a fifth embodiment of this invention.

A vitrectomy apparatus includes an external means 212, an infusion instrument 213 according to this invention and a cutter 214. The external means 212 is composed of an actuating unit 217 and a suction unit 218. The cutter 214 is equipped with a motor (not shown) so as to cut the vitreous body 3 by its inner blade means (not shown). A suction passage is placed in the cutter 214 and connected by way of a suction pipe 219 to the suction unit 218. The motor is connected through an electric cable 220 to the actuating unit 217.

Figure 12:
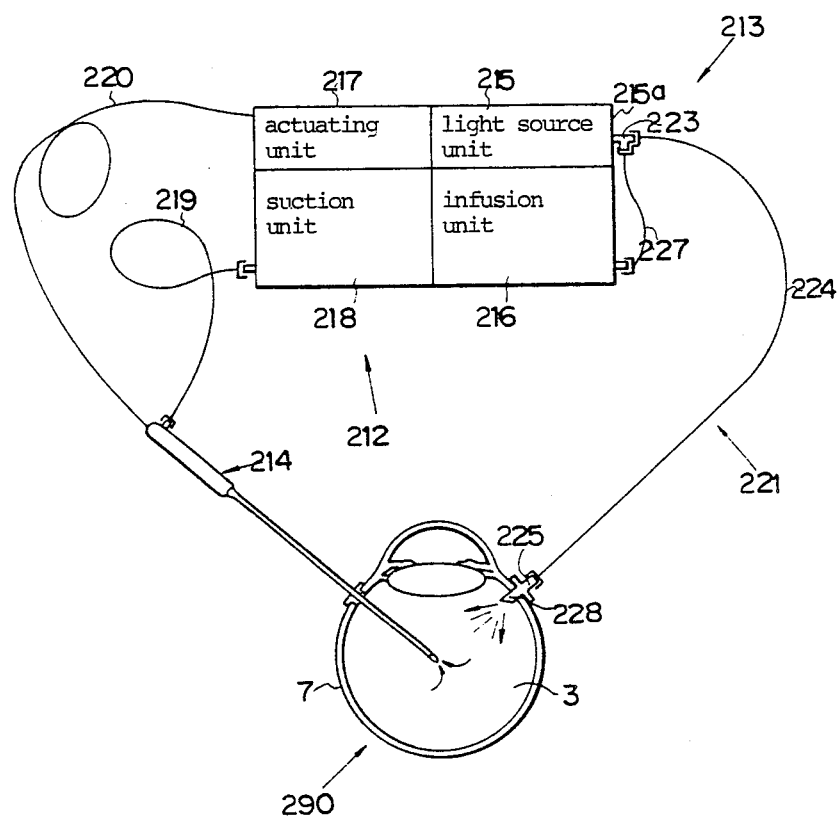
FIG. 12 is an explanatory view showing an operation condition in which an infusion instrument according to a fifth embodiment of this invention is used in vitrectomy.
Figure 17:
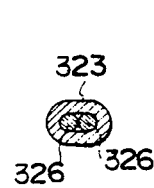
FIG. 17 is a sectional view taken along the line C—C of FIG.

The infusion instrument 213 includes a light source unit 215 equipped with a light source 270 therein, an infusion means 221 and two light transmitting means 222 as shown in FIGS. 12 and 13. The infusion means 221 has a T-shape in section of pipe-like first member 223, a pipe-like second member 224 and an insertion member 225. The second member 224 is preferably a tube made of a resilient material such as a silicon tube.

A joint portion 223a of the first member 223 is inserted into a side wall 215a of the light source unit 215. The two light transmitting means 222 are set at their input end 226 in the joint portion 223a.

Both input ends 226 face toward the light source 270 of the light source unit 215. A relay lens 280 is placed between the light source 270 and the input ends 226. An image from the light source 270 is projected at the input ends 226 by the relay lens 280. The light from the light source unit 215 is transmitted through the two transmitting means 222 each having no joint portion. The light transmitting means 22 are preferably optical fibers made of a glass or plastics.

The two light transmitting means 222 are arranged within the first member 223 and the second member 224. The input ends 226 of the light transmitting means 222 are arranged side by side in the joint portion 223a of the first member 223 as best shown in FIG. 14. They are freely placed within the second member 224 as best shown in FIG. 13. Thus, the two light transmitting means 222 substantially do not affect the resiliency or flexibility of the second member 224.

The connecting portion 223b of the first member 223 is connected by way of a connecting tube 227 to the infusion unit 216 as shown in FIGS. 12 and 13. The connecting portion 223c of the first member 223 is inserted into one end of the second member 224.

The insertion member 225 is located at the other end of the second member 224. The insertion end 228 of the insertion member 225 has an inclined end surface so as to be easily inserted into the scleral 7.

The insertion member 225 is inserted into the other end of the second member 224 so as to be connected tightly to both the output ends 229 of the light transmitting means 222. The insertion end 228 is cylindrical as best shown in FIG. 15. The insertion end 228 is preferably made of a transparent material such as plastics and has substantially the same refractive index of the light transmitting means 222. The outer surface of the insertion end 228 is coated with a material having a relatively small refractive index compared with a refractive index of a material of the insertion end 228. Therefore, the light is prevented from reflecting out of the outer surface of the insertion end 228 when it comes from the light transmitting means 222. Thus, the light coming through the insertion end 228 can reach the inside of the eyeball 290 without loss.

The insertion end 228 is partly surrounded by a tube 230 such as an infusion cannula having at its end a flange portion 230a made of an opaque material such as a metal for shielding the light. Four recesses 231 are formed in the flange portion 230a as shown in FIG. 15 for hooking strands or threads when the tube 230 is sutured to the scleral 7 of the eyeball 290.

The infusion passage 232 for carrying the intraocular irrigating solution from the infusion unit 216 into the eyeball 290 extends through the connecting tube 227, the first and second members 223, 224 and the insertion end 228.

In operation, the scleral 7 is incised at two portions thereof in such a manner that the cutter 214 and the insertion end 228 of the infusion means 221 can be inserted into the eyeball 290 therethrough. If desired, a further portion of the scleral 7 is incised for forceps and so on. The flange portion 230a is fixed to the scleral 7 by the threads or strands sutured thereto.

The light source 270 of the light source unit 215 is switched on to illuminate the inside of the eyeball 290 after the light therefrom is effectively transmitted through the two light transmitting means 222 and the insertion end 228. An opaque area of the vitreous body is cut by the cutter 214. The infusion unit 216 is actuated so as to infuse the intraocular irrigating solution through the infusion passage 232 and the insertion end 228 into the eyeball 290. Also, the suction unit 218 is actuated so as to suck both the cut portion and the intraocular irrigating solution through the cutter 214 and the pipe 219.

After the cutting and suction, the vitreous cavity is filled with the intraocular irrigating solution thereby to maintain a predetermined intraocular pressure therein.

At the end of the operation, the insertion end 228 and the cutter 214 are drawn out and then the incised portions are sutured.

No cover for the two light transmitting means 222 is additionally required because they are covered by the first and second members 223, 224. The insertion end 228 functions to infuse the intraocular irrigating solution into the eyeball 290 and constitutes an extending portion of the light transmitting means 222 so as to transmit the light. The light transmitting means 222 are not inserted into the eyeball 290.

EMBODIMENT 6

FIGS. 16 to 20 show a sixth embodiment of this invention which is substantially the same as the fifth embodiment of FIGS. 12 to 15 except for two light transmitting means 322 and a joint portion 352 of an insertion member 328 constituting an extending portion thereof. The same references designate the same or corresponding members or parts.

Figure 22:
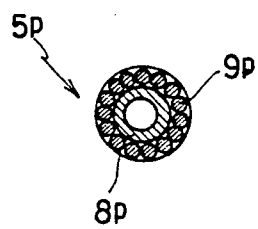

In the sixth embodiment of FIGS. 16 to 20, two input ends 126 of the two light transmitting means 322 are connected to a further single light transmitting means 400. Two output ends 329 of the two light transmitting means 322 are joined to one end of the insertion member 328. The sectional area of the insertion member 328 can be set relatively small as compared with that of the prior art of FIG. 22 because the sectional area of both the optical fiber bundles and the cover thereof can be eliminated. Thus, when the insertion member 328 is drawn out, collapse of the eye can be avoided. In addition, if the insertion member 328 is set small in size and light in weight, it can be directly sutured to the eyeball 390 whereby it is not necessary to support the infusion means 321 by a hand during operation.

The output end of the insertion member 328 can be apart from the eyegrounds if its length is set short. Thus, a wide area on the eyegrounds can be illuminated so that the operations become easy.

Figure 18:
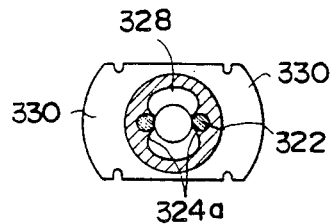
FIG. 18 is a sectional view taken along the line D—D of FIG. 16.
Figure 19:
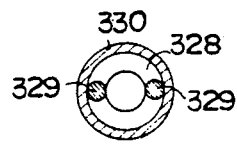
FIG. 19 is a sectional view taken along the line E—E of FIG. 16.
Figure 20:
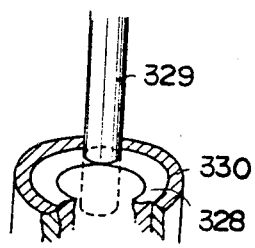
FIG. 20 is a perspective view showing a portion of the infusion means shown in FIG. 16, with some parts cut away.
Figure 21:
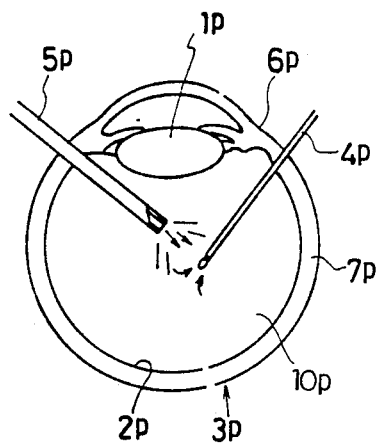

As shown in FIG. 18, the two light transmitting means 322 are placed in longitudinal grooves 324a formed in an inner wall of the second member 324. The output ends 329 of the light transmitting means 322 fixedly extend into the insertion member 328 as shown in FIGS. 19 and 20. Therefore, the relative position of the light transmitting means 322 to the insertion member 328 is fixed so as to transmit precisely the light into the eyeball.

A flange portion 330a of a tube 330 such as an infusion cannula is substantially the same as the flange portion 230a of the tube 230 in FIG. 13.

The input ends 326 of the light transmitting means 322 are arranged side by side in the first member 323 and connected tightly to the light transmitting means 400 of a large diameter by way of a connector 410. The light transmitting means 400 is connected to the light source unit 315. The light from the light source 370 comes into the light transmitting means 400 by a lens 380.

This invention is not limited to the above-stated embodiments. For instance, the light transmitting means 222 or 322 may be composed of three divided parts or more.

We claim:

1. An infusion instrument for use in vitrectomy comprising:
   an infusion having an input end, an insertion member for insertion into an eyeball and an infusion passage means connected between the input end and the insertion member so as to form a flow path for infusing an intraocular irrigating solution from the input end through the flowpath and through the insertion member into an eyeball;
   a source of fluid in fluid communication with the input end of the infusion means;
   the infusion passage means having a resilient portion made of a resilient material at least near the insertion member;
   an illumination unit including a light source for illuminating an inside portion of an eyeball; and
   a light transmitting means made of a resilient material and having an input end connected to the light source and an output end connected to the insertion member for receiving light entering through the input end from the light source and transmitting the light out of the output end to an interior portion of an eyeball, wherein at least a portion of the light transmitting means is arranged inside the flowpath located in the resilient portion of the infusion passage means; and
   the insertion member including attachment means, comprising a flange portion of the insertion member, for permitting attachment of the insertion member to an eyeball without additional support by an operator, wherein the insertion member comprises a connection portion located on one side of the flange portion, for connecting to the infusion passage means, and an insertion portion located on an opposite side of said flange portion, for insertion into an eyeball, said flowpath passing through both said connection portion and said insertion portion and wherein said light transmitting means terminates inside of said insertion portion.

2. An instrument as defined in claim 2, wherein a majority of the light transmitting means is placed inside the flowpath within the infusion passage means of the infusion means.

3. An instrument as defined in claim 1, wherein the light transmitting means comprises an optical fiber and the infusion passage means is tubular, and wherein the optical fiber is placed in the flowpath over substantially the full length of the infusion passage means.

4. An instrument as defined in claim 3, wherein the optical fiber is composed of a single body without any joint portion.

5. An instrument as defined in claim 4, wherein the illumination unit includes a relay means positioned between the light source and an input end of the optical fiber for guiding light from the light source into the optical fiber.

6. An instrument as claimed in claim 1, wherein said insertion portion has a diameter smaller than the diameter of said connection portion.

7. An instrument as defined in claim 1, wherein the flange portion has plural recesses for holding strands or threads for attaching the insertion member to the eyeball.

8. An instrument as defined in claim 1, wherein the light transmitting means is an optical fiber.

9. An infusion instrument for use in vitrectomy comprising:

an infusion means having an input end, an insertion member for insertion into an eyeball and an infusion passage means connected between the input end and the insertion member so as to form a flowpath for infusing an intraocular irrigating solution from the input end through the flowpath and through the insertion member into an eyeball;

a source of fluid in fluid communication with the input end of the infusion;

the infusion passage means having a resilient portion made of a resilient material at least near the insertion member;

an illumination unit including a light source for illuminating an inside portion of an eyeball; and a light transmitting means made of a resilient material and having an input end connected to the light source and an output end connected to the insertion member for receiving light entering through the input end from the light source and transmitting the light out of the output end to an interior portion of an eyeball, wherein at least a portion of the light transmitting means is arranged inside the flowpath located in the resilient portion of the infusion passage means; and the insertion member including attachment means, comprising a flange portion of the insertion member, for permitting attachment of the insertion member to an eyeball without additional support by an operator, wherein the insertion member comprises a connection portion located on one side of the flange portion, for connecting to the infusion passage means, and an insertion portion located on an opposite side of said flange portion, for insertion into an eyeball, said flowpath passing through both said connection portion and said insertion portion, and wherein the light transmitting means terminates within said connection portion of the insertion member.

10. An instrument as defined in claim 9, wherein the flowpath within said insertion member has an inner surface of a high reflectivity for reflecting light from said light transmitting means into the interior of an eyeball.

11. An instrument as defined in claim 9, wherein the light transmitting means is an optical fiber.

12. An instrument as defined in claim 9, wherein the flange portion has plural recesses for holding strands or threads for attaching the insertion member to the eyeball.

13. An infusion instrument for use in vitrectomy comprising:

an infusion means having an input end, an insertion member for insertion into an eyeball and an infusion passage means connected between the input end and the insertion member so as to form a flowpath for infusing an intraocular irrigating solution from the input end through the flowpath and through the insertion member into an eyeball;

a source of fluid in fluid communication with the input end of the infusion means;

the infusion passage means having a resilient portion made of a resilient material at least near the insertion member;

an illumination unit including a light source for illuminating an inside portion of an eyeball; and a light transmitting means made of a resilient material and having an input end connected to the insertion member for receiving light entering through the input end from the light source and transmitting the light out of the output end to an interior portion of an eyeball, wherein at least a portion of the light transmitting means is arranged inside the flowpath located in the resilient portion of the infusion passage means; and the insertion member including attachment means, comprising a flange portion of the insertion member, for permitting attachment of the insertion member to an eyeball without additional support by an operator, wherein the insertion member is comprised of a light transmitting material and is positioned at the output end of said light transmitting means and forms a continuation of said light transmitting means, and wherein the flowpath extends through said continuation of said light transmitting means.

14. An instrument as defined in claim 13, wherein the continuation of the light transmitting mean formed by said insertion member of light transmitting material is coated with a material having a smaller index of refraction than that of the light transmitting material, whereby the insertion member acts as an optical wave guide.

15. An instrument as defined in claim 14, wherein the insertion member further comprises a surrounding member which includes said flange portion and which is made of an opaque material.

16. An instrument as defined in claim 13, wherein the insertion member comprises a diagonal bevel on its insertion end for providing greater illumination to an eyeball interior.

17. An instrument as claimed in claim 13, wherein said light transmitting means is inserted into a deadened recess formed in the light transmitting material of said insertion member.

18. An instrument as claimed 13, wherein said light transmitting means comprises plural optical fibers.

19. An instrument as defined in claim 13, wherein the flange portion has plural recesses for holding strands or threads for attaching the insertion member to the eyeball.

20. An infusion instrument for use in vitrectomy comprising:

an infusion means having an input end, an insertion member for insertion into an eyeball and an infusion passage means connected between the input end and the insertion member so as to form a flowpath for infusing an insertion member so as to form a flowpath for infusing an intraocular irrigating solution from the input end through the flowpath and through the insertion member into an eyeball;

a source of fluid in fluid communication with the input end of the infusion means;

the infusion passage means having a resilient portion made of a resilient material at least near the insertion member;

an illumination unit including a light source for illuminating an inside portion of an eyeball; and a light transmitting means made of a resilient material and having an input end connected to the light source and an output end connected to the insertion member for receiving light entering through the input end from the light source and transmitting the light out of the output end to an interior portion of an eyeball, wherein at least a portion of the light transmitting means is arranged inside the flowpath located in the resilient portion of the infusion passage means; and the insertion member including attachment means, comprising a flange portion of the insertion member, for permitting attachment of the insertion member to an eyeball without additional support by an operator, wherein the light transmitting means terminates within the infusion passage of the infusion means.

* * * * *